United States Patent
Matsumoto

(10) Patent No.: US 10,564,654 B2
(45) Date of Patent: Feb. 18, 2020

(54) LOOP INJECTION MECHANISM

(71) Applicant: Shimadzu Corporation, Kyoto (JP)

(72) Inventor: Keiko Matsumoto, Kyoto (JP)

(73) Assignee: Shimadzu Corporation, Nishinokyo-Kuwabaracho, Nakagyo-ku, Kyoto-shi, Kyoto (JP)

(*) Notice: Subject to any disclaimer, the term of this patent is extended or adjusted under 35 U.S.C. 154(b) by 116 days.

(21) Appl. No.: 15/899,832

(22) Filed: Feb. 20, 2018

(65) Prior Publication Data

US 2018/0267511 A1 Sep. 20, 2018

(30) Foreign Application Priority Data

Mar. 15, 2017 (JP) .................. 2017-050552

(51) Int. Cl.
*G05D 7/06* (2006.01)
*G01N 30/20* (2006.01)
*G01N 30/02* (2006.01)

(52) U.S. Cl.
CPC .......... *G05D 7/0658* (2013.01); *G01N 30/20* (2013.01); *G01N 2030/027* (2013.01); *G01N 2030/201* (2013.01); *G01N 2030/207* (2013.01)

(58) Field of Classification Search
None
See application file for complete search history.

(56) References Cited

U.S. PATENT DOCUMENTS

| 2008/0053543 A1* | 3/2008 | Baier ............. G01N 30/20 137/625.15 |
| 2010/0077874 A1 | 4/2010 | Kanomata |
| 2012/0203531 A1* | 8/2012 | Bisschops ......... B01D 15/1828 703/11 |

FOREIGN PATENT DOCUMENTS

JP 4675406 B2 4/2011

* cited by examiner

*Primary Examiner* — Sean Shechtman
(74) *Attorney, Agent, or Firm* — Muir Patent Law, PLLC

(57) ABSTRACT

A flow path switching unit switches a flow path to an introduction state for introducing a sample in a sample loop, an analysis state for flowing a mobile phase into a column via the sample loop, or a cleaning state for introducing a cleaning solution into a sample loop. A command execution processing unit executes a plurality of preset control commands. A selection acceptance processing unit accepts a selection as to whether or not to switch the flow path from the analysis state to the cleaning state. In the case in which the selection of switching the flow path from the analysis state to the cleaning state is accepted by the selection acceptance processing unit, the command setting processing unit automatically includes the first switching command for switching the flow path from the analysis state to the cleaning state and the second switching command for returning the flow path from the cleaning state to the analysis state in a plurality of control commands.

12 Claims, 8 Drawing Sheets

|    | Command |
|----|---------|
| 1  | d.rinse |
| 2  | vial.n rn.sn |
| 3  | v.load |
| 4  | air.a av.ss |
| 5  | n.strk ns |
| 6  | aspir iv.ss |
| 7  | air.a av.ss |
| 8  | d.rinse |
| 9  | inj.p |
| 10 | disp iv.ds |
| 11 | s.inj |
| 12 | wait.sec 60 |
| 13 | v.load |
| 14 | purge.ml mv.rs |
| 15 | purge.rp rv.rs |
| 16 | wait.rt 0 |
| 17 | v.inj |
| 18 | wait.sec 60 |
| 19 | end |

FIG. 6

|    | Command |
|----|---------|
| 1  | d.rinse |
| 2  | vial.n rn.sn |
| 3  | v.load |
| 4  | air.a av.ss |
| 5  | n.strk ns |
| 6  | aspir iv.ss |
| 7  | air.a av.ss |
| 8  | d.rinse |
| 9  | inj.p |
| 10 | disp iv.ds |
| 11 | s.inj |
| 12 | wait.sec 60 |
| 13 | v.load |
| 14 | purge.ml mv.rs |
| 15 | purge.rp rv.rs |
| 16 | wait.rt 3 |
| 17 | v.inj |
| 18 | end |

FIG. 7

LOOP INJECTION MECHANISM

TECHNICAL FIELD

The present invention relates to a loop injection mechanism for introducing a part of a sucked sample into a sample loop and supplying it to a column together with a mobile phase.

BACKGROUND ART

For example, in a supercritical fluid chromatograph, a sample is injected by a loop injection method (see, for example, Japanese Patent No. 4675406 herein incorporated by reference). In a loop injection method, a sample is introduced into a sample loop, then a flow path is switched to supply a mobile phase in the sample loop, so that the sample in the sample loop can be flowed into a column together with the mobile phase. At this time, using a flow path switching unit such as a six-way valve, the flow path is switched between an introduction state for introducing the sample into the sample loop and an analysis state for flowing the mobile phase to a column via the sample loop.

In a loop injection mechanism that supplies a sample to a column with such a loop injection method, when cleaning the inside of the sample loop, the flow path is switched to a cleaning state in which a cleaning solution is flowed into the sample loop. By washing the inside of the sample loop in this cleaning state and then switching the flow path to the analysis state again, it is possible to completely remove the sample in the sample loop to thereby prevent occurrence of a phenomenon (so-called carry over) in which a peak based on the previous sample component appears at the next analysis.

In the case of automatically switching the flow path, a plurality of control commands to be given to a control unit is preset by a user, and the flow path is switched by sequentially executing the preset plurality of control commands by the control unit. In a conventional loop injection mechanism, such setting of control commands is performed by a user by arbitrarily selecting and combining a plurality of control commands.

SUMMARY OF THE INVENTION

Problems to be Solved by the Invention

However, since the aforementioned setting of control commands is confusing for an inexperienced user, there are cases that setting is erroneously set or inappropriate setting is performed in some cases. For example, when a user forgot to set a command to switch the path to the cleaning state, carryover may occur at the next analysis. Further, even in the case in which a command to switch the flow path to the cleaning state is set, if the setting of the switching timing is not appropriate, there is a risk of adversely affecting the detection result of the sample in the detector.

The present invention was made in view of the aforementioned circumstances, and an object thereof is to provide a loop injection mechanism capable of easily setting a control command.

A loop injection mechanism according to some embodiments of the present invention is equipped with a sample loop, a mobile phase supply unit, a column, a flow path switching unit, a command execution processing unit, a selection acceptance processing unit, and a command setting processing unit. A sample supply unit supplies a sample. A sample is introduced into the sample loop. The mobile phase supply unit supplies a mobile phase into the sample loop. A sample flows into the column from the sample loop together with the mobile phase. The flow path switching unit switches the flow path to an introduction state for introducing the sample in the sample loop, an analysis state for flowing a mobile phase into the column via the sample loop, or a cleaning state for introducing a cleaning solution into the sample loop. The command execution processing unit executes a plurality of preset control commands. The selection acceptance processing unit accepts a selection as to whether or not to switch the flow path from the analysis state to the cleaning state. The command setting processing unit automatically includes, when a selection of switching the flow path from the analysis state to the cleaning state is accepted by the selection acceptance processing unit, a first switching command for switching the flow path from the analysis state to the cleaning state and a second switching command for returning the flow path from the cleaning state to the analysis state in the plurality of control commands.

According to such a configuration, a mere selection by a user as to whether or not to switch the flow path from the analysis state to the cleaning state enables automatic setting of a plurality of control commands including a first switching command and a second switching command. That is, it is unnecessary for a user to perform an operation of selecting and combining the first switching command and the second switching command, and it is only necessary for the user to select whether or not to perform switching of the flow path from the analysis state to the cleaning state. For this reason, it is easy even for an inexperienced user to understand, which enables easy setting of control commands.

In some examples the selection acceptance processing unit may be configured to accept, when a selection of switching the flow path from the analysis state to the cleaning state is accepted, a selection as to whether or not to automatically set a start time of switching the flow path from the analysis state to the cleaning state and an end time of returning the flow path from the cleaning state to the analysis state.

According to such a configuration, in the case in which a user selects to switch the flow path from the analysis state to the cleaning state, it is possible to further select whether or not to automatically set the start time and the end time of switching the flow path. In the case in which a user selects to automatically set the start time and the end time, it is not necessary for the user to set the start time and the end time. As a result, the setting of control commands can be more easily set.

In some examples the command setting processing unit may be configured to automatically include, when a selection of automatically setting the start time and the end time is accepted by the selection acceptance processing unit, an automatic start command for setting a time when a first waiting time has elapsed with respect to a time when the flow path is switched from the introduction state to the analysis state as the start time in the plurality of control commands.

According to such a configuration, in the case in which a user selects to automatically set the start time and the end time, a more appropriate start time can be automatically set. Specifically, since the time when the first waiting time has elapsed with respect to a time when the flow paths is switched from the introduction state to the analysis state, after a sample is completely flowed out of the sample loop, the flow path can be switched from the analysis state to the cleaning state to flow the cleaning solution into the sample loop.

In some examples the command setting processing unit may be configured to automatically include, when a selection of automatically setting the start time and the end time is accepted by the selection acceptance processing unit, an automatic end command for setting a time when a preset analysis is completed as the end time in the plurality of control commands.

According to such a configuration, in the case in which a user selects to automatically set a start time and an end time, a more appropriate end time can be set automatically. Specifically, since the time when a preset analysis is completed is set as an end time, it will not happen that the state is returned from the cleaning state to the analysis state in the middle of the detection of the sample by the detector, causing the cleaning solution in the sample loop to reach the detector together with each sample component, which results in an adverse effect on the detection result.

In some examples the command setting processing unit may be configured to automatically include a standby command for starting a next analysis after a second waiting time has elapsed with respect to the end time in the plurality of control command.

According to such a configuration, in the case in which a user selects to automatically set a start time and an end time, it will not happen that the next analysis will be initiated after returning from the cleaning state to the analysis state at the time when a preset analysis is completed before elapsing the second waiting time. With this, it is possible to initiate the next analysis after the cleaning solution in the sample loop has completely passed through the column. Therefore, it will not happen that the cleaning solution adversely affects the detection result at the next analysis.

In some examples the loop injection mechanism includes a time input acceptance processing unit configured to accept an input of the start time and the end time when a selection of not automatically setting the start time and the end time is accepted by the selection acceptance processing unit. In this case, it may be configured such that the command setting processing unit automatically includes, when an input of the start time and the end time is accepted by the time input acceptance processing unit, an individual start command for executing the first switching command when the start time has elapsed with respect to a time when the flow path is switched from the introduction state to the analysis state, and an individual termination command for executing the second switching command when the end time has elapsed with respect to a time when the flow path is switched from the introduction state to the analysis state in the plurality of control commands.

According to such a configuration, in the case in which a user selects not to automatically set the start time and the end time, the user can arbitrarily set the start time and the end time. Therefore, the user can individually set the more appropriate start time and end time by setting the start time and the end time by, e.g., confirming the detection result in the detector.

Accordingly, it may be unnecessary for a user to perform an operation of selecting and combining the first switching command and the second switching command, and it may only be necessary to perform a selection as to whether or not to switch the flow path from the analysis state to the cleaning state. For this reason, it is easy even for an inexperienced user to understand, and the setting of control commands can be easily set.

BRIEF DESCRIPTION OF THE DRAWINGS

FIG. 6 is a diagram showing one example of a combination of control commands to be set by a command setting processing unit, and shows a case in which it is selected to automatically set the start time and the end time.

FIG. 7 is a diagram showing another example of a combination of control commands to be set by a command setting processing unit, and shows a case in which it is not selected to automatically set the start time and the end time.

EMBODIMENTS FOR CARRYING OUT THE INVENTION

1. Overall Configuration of Loop Injection Mechanism

Figure 1:
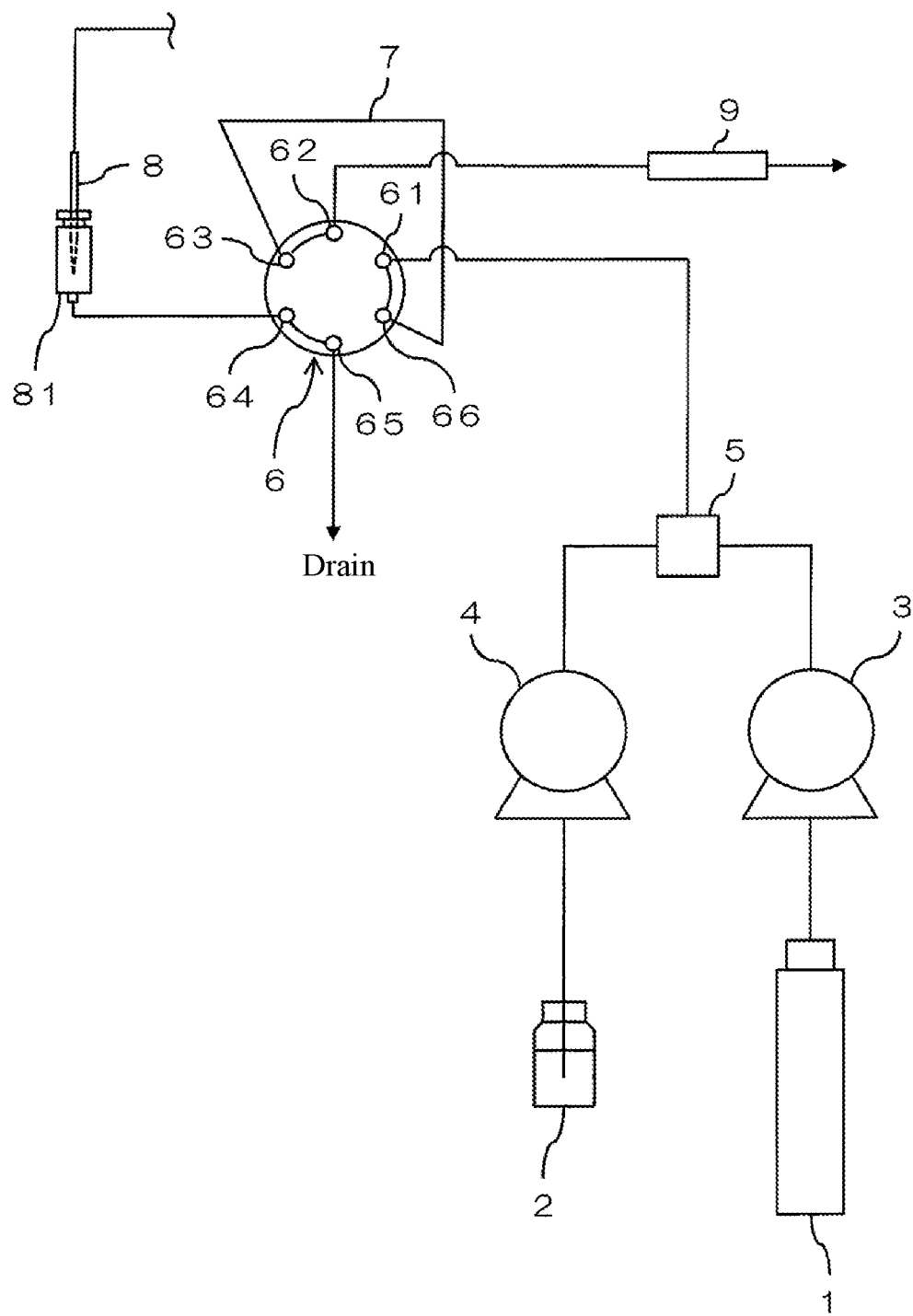
FIG. 1 is a flow path diagram of a loop injection mechanism according to one embodiment of the present invention, and shows a case in which a flow path is in an analysis state.

FIG. 1 is a flow path diagram of a loop injection mechanism according to an embodiment of the present invention, and shows the case in which a flow path is in an analysis state. This loop injection mechanism is used for, e.g., a supercritical fluid chromatograph to inject a sample into a column 9 by a loop injection method. The loop injection mechanism is equipped with a mobile phase reservoir 1, a modifier reservoir 2, a first pump 3, a second pump 4, a mixer 5, a six-way valve 6, a sample loop 7, a needle 8, etc.

In the mobile phase reservoir 1, carbon dioxide as a mobile phase is stored in a liquid state. Further, a modifier solution is stored in the modifier reservoir 2. The modifier solution is composed of an organic solvent, such as, e.g., ethanol and methanol. The mobile phase in the mobile phase reservoir 1 is sent out by the first pump 3, and is mixed, in the mixer 5, with the modifier solution sent out from the modifier reservoir 2 by the second pump 4. The mobile phase mixed with the modifier solution is sent from the mixer 5 to a six-way valve 6. At this time, the carbon dioxide as a mobile phase is maintained in the supercritical state by the back pressure.

The six-way valve 6 is equipped with six ports 61 to 66 composed of a first port 61, a second port 62, a third port 63, a fourth port 64, a fifth port 65, and a sixth port 66, and can switch the connection state of these ports 61 to 66. The mixer 5 is connected to the first port 61, and the mobile phase flows from the first port 61 into the six-way valve 6. The second port 62 is connected to the column 9.

One end of the sample loop 7 is connected to the third port 63, and the other end of the sample loop 7 is connected to the sixth port 66. A sample is introduced into the sample loop 7, and the sample loop 7 into which the sample was introduced is connected to the column 9 via the third port 63 and the second port 62 as shown in FIG. 1, so that the sample in the sample loop 7 flows into the column 9 together with the mobile phase. At this time, the mobile phase reservoir 1, the modifier reservoir 2, and the mixer 5 configure a mobile phase supply unit for supplying the mobile phase into the sample loop 7 via the first port 61 and the sixth port 66.

An injection port 81 is connected to the fourth port 64. The injection port 81 is configured so as to be connected by a movable needle 8, and the sample sucked from a sample container (not illustrated) can be injected into the injection port 81 by the needle 8. The fifth port 65 is served as a drain port for drainage.

2. Switching of Flow Paths

Figure 2:
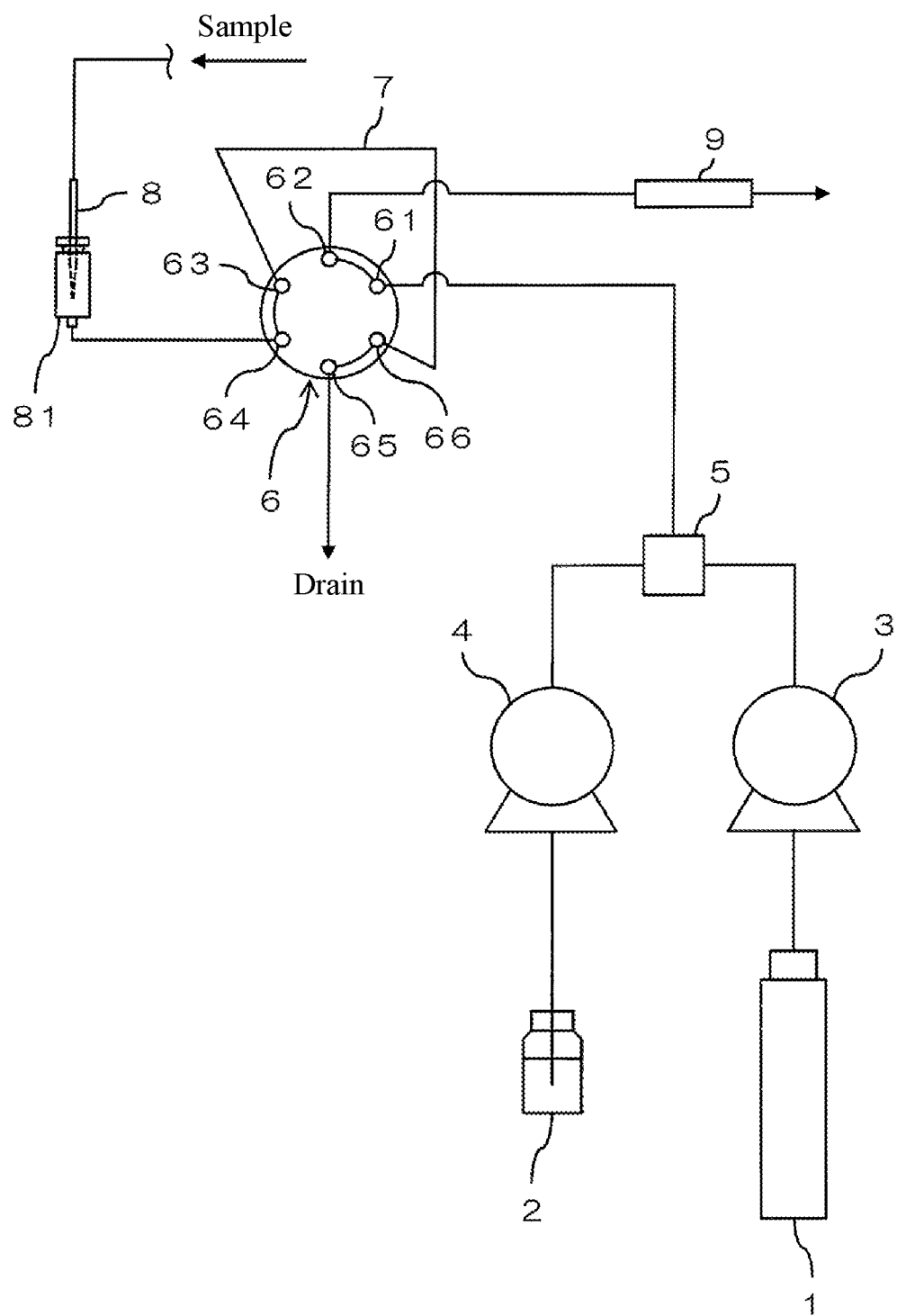
FIG. 2 is a flow path diagram of a loop injection mechanism, and shows a case in which a flow path is in an introduction state.
Figure 3:
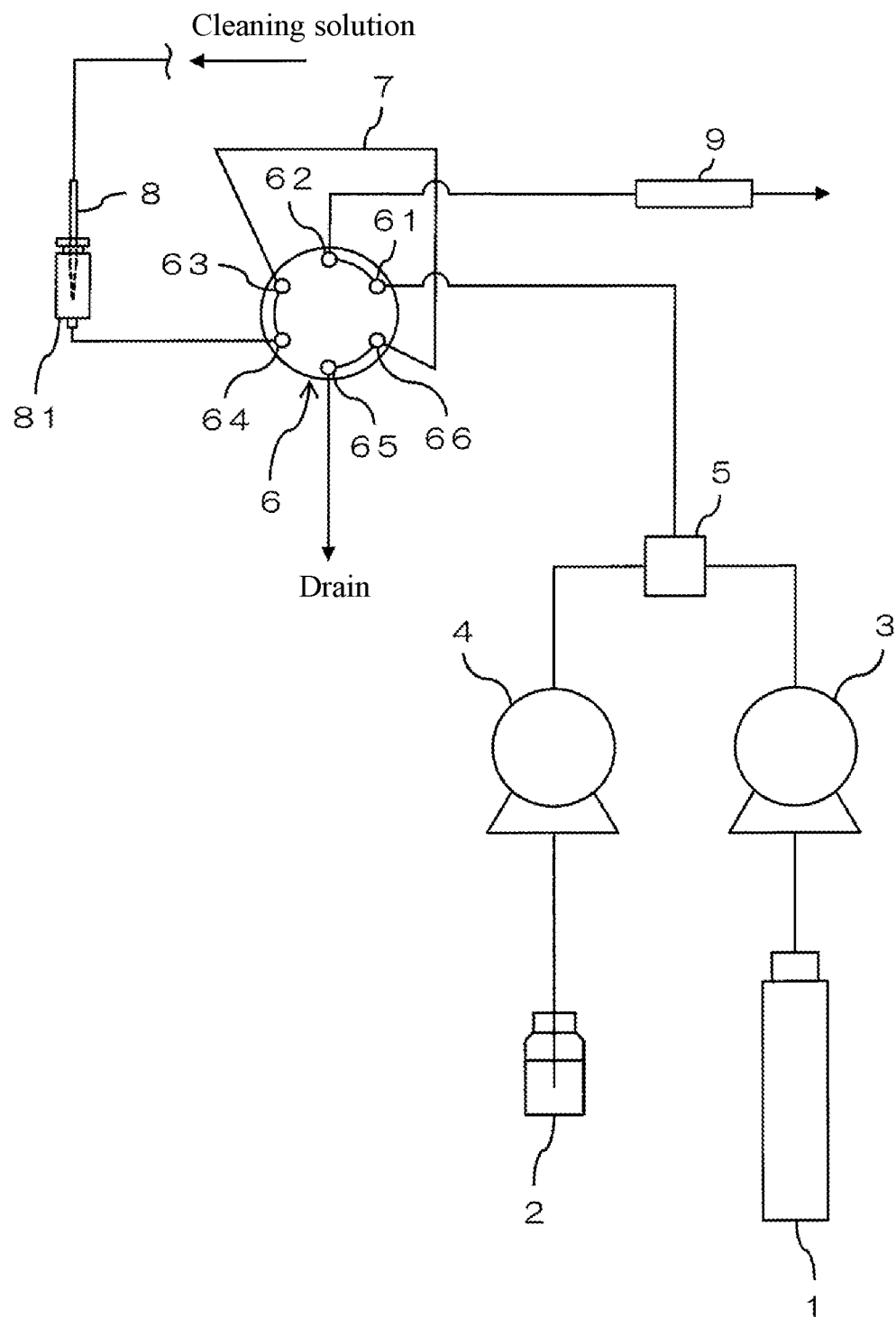
FIG. 3 is a flow path diagram of a loop injection mechanism, and shows a case in which a flow path is in a cleaning state.

FIGS. 2 and 3 are flow path diagrams of the loop injection mechanism. FIG. 2 shows a case in which the flow path is in an introduction state. FIG. 3 shows a case in which the flow path is in a cleaning state. In this embodiment, by switching the connection state of the ports 61 to 66 in the six-way valve 6, it becomes one of the analysis state shown in FIG. 1, the introduction state shown in FIG. 2, and the cleaning state shown in FIG. 3. That is, the six-way valve 6 comprises a flow path switching unit for switching the flow path to the analysis state, the introduction state, or the cleaning state.

In the introduction state shown in FIG. 2, the first port 61 and the second port 62 of the six-way valve 6 are connected, so that the flow path of the mobile phase communicating with the column 9 is separated from the sample loop 7. On the other hand, the third port 63 and the fourth port 64 are connected and the fifth port 65 and the sixth port 66 are connected, so that one end of the sample loop 7 communicates with the injection port 81 and the other end communicates with the drain port.

When introducing a sample into the sample loop 7, a needle 8 is inserted into the sample container in advance, and a sample is sucked into the needle 8 by a driving pump (not illustrated) communicating with the needle 8. Thereafter, as shown in FIG. 2, the needle 8 is connected to the injection port 81, and the sample is injected from the needle 8 into the injection port 81 by driving a pump. As a result, the sample is introduced into the sample loop 7 from the injection port 81 through the fourth port 64 and the third port 63.

After introducing the sample into the sample loop 7, the flow path is switched using the six-way valve 6. As a result, the introduction state shown in FIG. 2 is switched to the analysis state shown in FIG. 1. That is, one end of the sample loop 7 communicates with the column 9 via the third port 63 and the second port 62, and the other end thereof communicates with the mixer 5 via the sixth port 66 and the first port 61. As a result, the sample loop 7 is interposed in the flow path of the mobile phase communicating with the column 9, so that the sample in the sample loop 7 flows into the column 9 together with the mobile phase. The sample is separated into each of sample components in the process of passing through the column 9, and each separated sample component is detected by a detector (not illustrated).

After the flow path is switched from the introduction state to the analysis state as described above, the flow path is switched at a preset timing using the six-way valve 6, so that the analysis state is switched to the cleaning state shown in FIG. 3. That is, the third port 63 and the fourth port 64 are connected and the fifth port 65 and the sixth port 66 are connected, so that one end of the sample loop 7 communicates with the injection port 81 and the other end communicates with the drain port. As a result, the flow path of the mobile phase communicating with the column 9 will be separated again from the sample loop 7.

In the cleaning state shown in FIG. 3, the needle 8 is connected to the injection port 81. In this state, the pump described above is driven, so that the cleaning solution is injected into the injection port 81 from a cleaning solution reservoir (not illustrated) via the needle 8. The cleaning solution injected into the injection port 81 flows into the sample loop 7 via the fourth port 64 and the third port 63 and then drained from the drain port via the sixth port 66 and the fifth port 65. As a result, the inside of the sample loop 7 is cleaned with the cleaning solution.

After the inside of the sample loop 7 is cleaned as described above, the flow path is switched using the six-way valve 6 at a preset timing, so that the cleaning state shown in FIG. 3 is switched to the analysis state shown in FIG. 1. That is, one end of the sample loop 7 communicates with the column 9 via the third port 63 and the second port 62, and the other end thereof communicates with the mixer 5 via the sixth port 66 and the first port 61. At this time, the sample loop 7 is interposed in the flow path of the mobile phase communicating with the column 9, so that the cleaning solution remained in the sample loop 7 flows into the column 9 for a certain period of time.

3. Electrical Configuration and Setting Method of Loop Injection Mechanism

Figure 4:
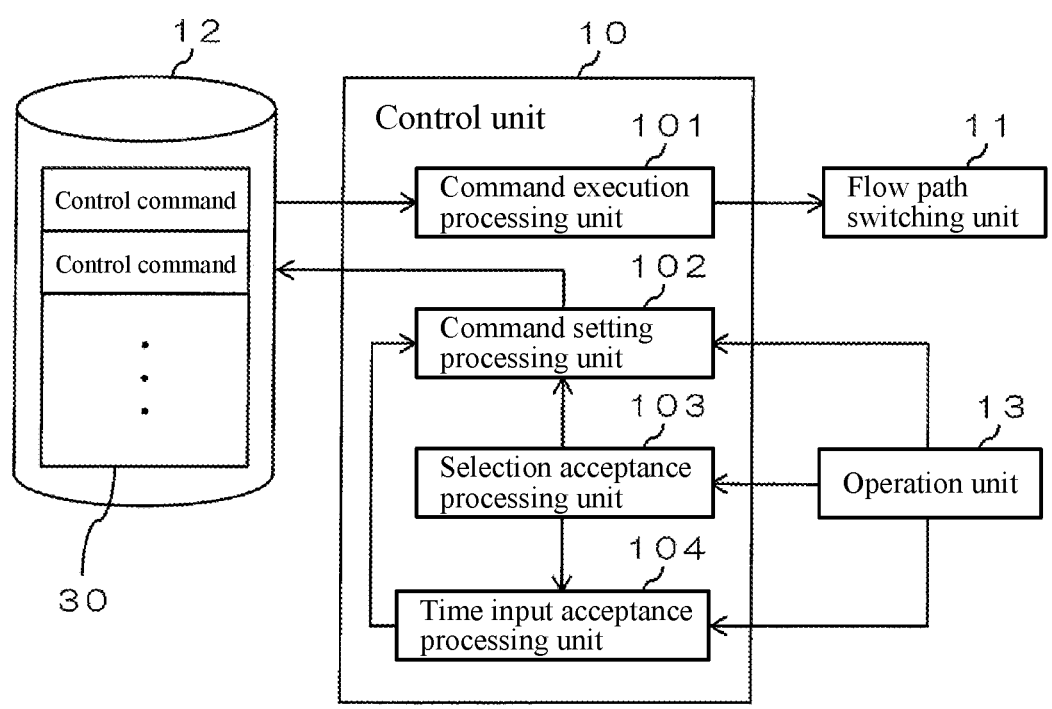
FIG. 4 is a block diagram showing one example of an electrical configuration of a loop injection mechanism.

FIG. 4 is a block diagram showing one example of an electrical configuration of a loop injection mechanism. The loop injection mechanism according to this embodiment includes a control unit 10, a flow path switching unit 11, a storage unit 12, an operation unit 13, and the like. The control unit 10 may be a computer and include, for example, one or more processors configured by software, such as a CPU (Central Processing Unit) GPU, controller, etc., and include a command execution processing unit 101, a command setting processing unit 102, a selection acceptance processing unit 103, a time input acceptance processing unit 104, and the like, forming various functional modules of the computer. The computer may be a general purpose computer or may be dedicated hardware or firmware (e.g., an electronic or optical circuit, such as application-specific hardware, such as, for example, a digital signal processor (DSP) or a field-programmable gate array (FPGA)). Each functional module (or unit) described herein may comprise a separate computer, or some or all of the functional module (or unit) may be comprised of and share the hardware of the same computer. Connections and interactions between the units described herein may be hardwired and/or in the form of data (e.g., as data stored in and retrieved from memory of the computer, such as a register, buffer, cache, storage drive, etc., such as part of an application programming interface (API)). The functional modules (or units) of control unit 10 (e.g., 101, 102, 103 and 104) may correspond to separate segment or segments of software (e.g., a subroutine) which configure the computer of the control unit 10, or may correspond to segment(s) of software that also correspond to one or more other functional modules (or units) described herein. As is understood, "software" refers to prescribed rules to operate a computer, such as code or script. Storage 12 may comprise conventional memory of a computer, such as a hard drive (which may be a solid state drive, DRAM, NAND flash memory, etc.). Operation unit 13 may comprise a conventional computer user interface and include convention input devices, such as a keyboard, mouse, trackpad, touchscreen, etc.

The command execution processing unit 101 controls the operation of each part of the loop injection mechanism by executing a plurality of preset control commands 30. The plurality of control commands 30 are stored in advance in the storage unit 12 together with their execution order, and the command execution processing unit 101 sequentially executes each control command 30, so that the operation of, e.g., the flow path switching unit 11 including the six-way valve 6 is automatically controlled.

The command setting processing unit 102 sets the plurality of control commands 30 together with the execution order and makes the storage unit 12 store the control commands. The setting of the control commands 30 is performed based on the operation of the operation unit 13 by a user. In other words, a user can set commands by arbitrarily selecting a plurality of control commands 30 through the operation of the operation unit 13, and combining the control commands 30 in an arbitrary execution order.

The selection acceptance processing unit 103 accepts a selection as to whether or not to switch the flow path from the analysis state shown in FIG. 1 to the cleaning state shown in FIG. 3 based on the operation of the operation unit 13 by the user. It is not easy for a user to perform the operation of selecting a plurality of control commands 30 and combining the selected control commends as described above. Therefore, in this embodiment, in the case in which the selection of switching the flow path from the analysis state to the cleaning state is accepted by the selection acceptance processing unit 103, it is configured such that control commands 30 necessary for the switching is automatically set by the command setting processing unit 102.

In particular, a control command 30 (first switching command) for switching the flow path from the analysis state shown in FIG. 1 to the cleaning state shown in FIG. 3 and a control command 30 (second switching command) for returning the flow path from the cleaning state shown in FIG. 3 to the analysis state shown in FIG. 1 are automatically included in a plurality of control commands 30 to be set by the command setting processing unit 102. Such setting for automatically including the first switching command and the second switching command in a plurality of control commands 30 is called "cut-off loop setting" in this embodiment.

Figure 5:
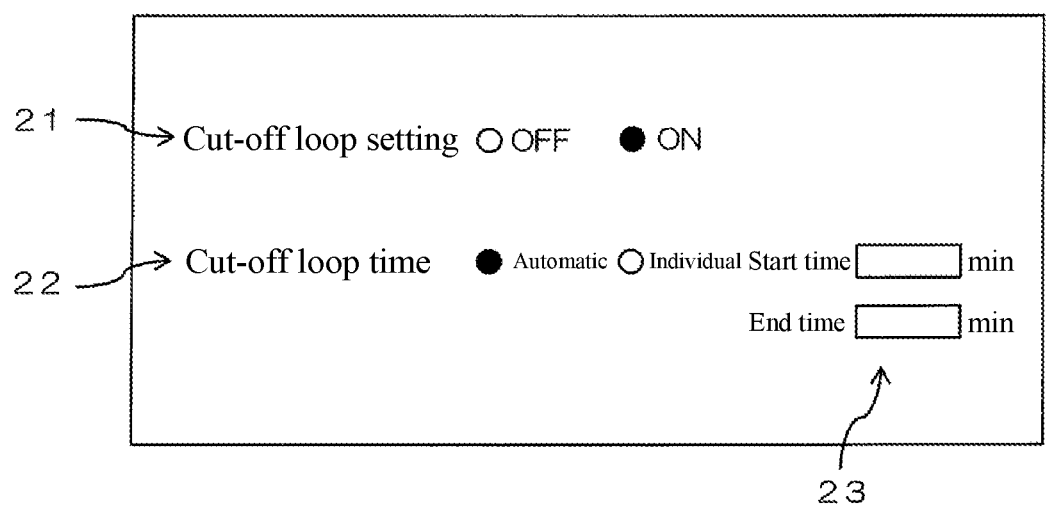
FIG. 5 is a diagram showing one example of a setting screen for cut-off loop setting.

FIG. 5 is a diagram showing one example of a setting screen for the cut-off loop setting. The setting screen may be part of the user interface of the operation unit 13 and may be a touch screen or otherwise interact with a user input (e.g., trackpad or mouse) to allow selections corresponding to its displayed image elements. This setting screen includes a setting selection section 21 for selecting whether or not to set the cut-off loop and a time selection section 22 for selecting whether or not to automatically set the time when performing the cut-off loop setting.

In the setting selection section 21, the setting in which the cut-off loop setting is not performed (OFF setting) is set as default. By performing a selection operation in the setting selection section 21 using the operation unit 13, a user can switch the setting to a setting (ON setting) in which the cut-off loop setting is performed as shown in FIG. 5. With this, a selection of switching the flow path from the analysis state to the cleaning state is accepted by the selection acceptance processing unit 103, which enables the selection operation in the time selection section 22.

In the time selection section 22, it is possible to select whether or not to automatically set the time (start time) to switch the flow path from the analysis state to the cleaning state and the time (end time) to return the flow path from the cleaning state to the analysis state. When a user performs a selection operation of the time selection section 22 using the operation unit 13, a selection as to whether or not to automatically set the start time and the end time is accepted by the the selection acceptance processing unit 103. In the time selection section 22, as shown in FIG. 5, the setting for automatically setting the start time and the end time is set as default.

In the case in which "Automatic" is selected in the time selection section 22 and therefore it is selected to automatically set the start time and the end time, the command setting processing unit 102 performs the processing of automatically including the control command 30 (automatic start command) for setting a predetermined time as a start time and the control command 30 (automatic end command) for setting a predetermined time as an end time in the plurality of control commands 30.

On the other hand, in the case in which "Individual" is selected in the time selection section 22 and therefore it is selected not to automatically set the start time and the end time, a user performs an input operation to the time input unit 23 for inputting the start time and the end time by operating the operation unit 13. At this time, the input of the start time and the end time for the time input unit 23 is accepted by the time input acceptance processing unit 104, and command setting by the command setting processing unit 102 is performed based on the start time and the end time. That is, the command setting processing unit 102 performs the processing of automatically including a control command 30 (individual start command) for executing the first switching command when the input start time has elapsed, a control command 30 (individual termination command) for executing the second switching command when the input end time has elapsed, etc., in the plurality of control commands 30.

4. Specific Example of Control Command

FIG. 6 is a diagram showing one example of a combination of control commands 30 to be set by the command setting processing unit 102, and shows the case in which it is selected to automatically set the start time and the end time.

In the setting selection section 21 shown in FIG. 5, in the case in which the selection of switching the flow path from the analysis state to the cleaning state (ON setting of the cut-off loop setting) is performed, the first switching command 31 for switching the flow path from the analysis state to the cleaning state and the second switching command 32 for returning the flow path from the cleaning state to the analysis state are automatically included in the plurality of control commands 30 to be set by the command setting processing unit 102.

As described above, a mere selection by a user as to whether or not to switch the flow path from the analysis state to the cleaning state in the setting selection section 21 enables automatic setting of a plurality of control commands including the first switching command and the second switching command. That is, it is unnecessary for a user to perform an operation of selecting and combining the first switching command 31 and the second switching command 32 and it is only necessary to select whether or not to switch the flow path from the analysis state to the cleaning state. For this reason, it is easy even for an inexperienced user to understand, and the setting of control commands 30 can be easily set.

Thereafter, "Automatic" or "Individual" is selected in the time selection section 22 shown in FIG. 5. That is, in the case in which a user selects to switch the flow path from the analysis state to the cleaning state in the setting selection section 21, it is possible to further select in the time selection section 22 whether or not to automatically set the start time and the end time of switching the flow path of the flow path. In the case in which "Automatic" is selected in the time selection section 22 and therefore it is selected to automatically set the start time and the end time, the automatic start command 33 and the automatic end command 34 are automatically included in the plurality of control commands 30 to be set by the command setting processing unit 102. In this case, it becomes unnecessary for a user to set the start time and the end time by himself/herself, so the setting of the control commands 30 can be performed more easily.

The automatic start command 33 is a control command 30 for setting the time when the first waiting time (for example, 60 seconds) has elapsed with respect to the time when the flow path is switched from the introduction state to the analysis state as the time (start time) to switch the flow path from the analysis state to the cleaning state. When the time when the first waiting time has elapsed with respect to a time when the flow path is switched from the introduction state to the analysis state, after a sample completely flowed out of the sample loop 7, the flow path can be switched from the analysis state to the cleaning state to flow the cleaning solution in the sample loop. Therefore, a more appropriate start time can be set automatically.

The automatic end command 34 is a control command 30 for setting the time when the preset analysis is completed as the time (end time) for returning the flow path from the cleaning state to the analysis state. The time when the analysis is completed is automatically determined based on preset analysis conditions. By setting the time when the preset analysis is completed as an end time, it will not happen such that the cleaning state is returned to the analysis state in the middle of the detection of the sample by the detector, causing the cleaning solution in the sample loop to reach the detector together with each sample component, which results in an adverse effect on the detection result. Therefore, a more appropriate end time can be set automatically.

In the case in which the automatic end command 34 is set, a control command 30 (standby command 35) for starting the next analysis after the second waiting time (for example, 60 seconds) has elapsed with respect to the end time is automatically included in the plurality of control commands 30 to be set by the command setting processing unit 102. In this case, it will not happen that the next analysis will be initiated after returning from the cleaning state to the analysis state at the time when a preset analysis is completed before elapsing the second waiting time. With this, it is possible to initiate the next analysis after the cleaning solution in the sample loop 7 has completely passed through the column 9. Therefore, it will not happen that the cleaning solution adversely affects the detection result at the next analysis. Instead of automatically including the standby command 35 at the end of the control command 30 as shown in FIG. 6, it may be configured such that the standby command 35 is automatically included at the beginning of each control command. Also in this case, even if a cleaning solution remains in the column 9 in the previous analysis, at the start of the next analysis, since the next analysis can be started after the cleaning solution in the sample loop 7 has completely passed through the column 9, the cleaning solution does not adversely affect the detection result at the next analysis.

FIG. 7 is a diagram showing another example of a combination of control commands 30 to be set by the command setting processing unit 102, and shows the case in which it is selected not to automatically set the start time and the end time.

In the setting selection section 21 shown in FIG. 5, in the case in which the selection of switching the flow path from the analysis state to the cleaning state (ON setting of cut-off loop setting) is performed, the first switching command 31 for switching the flow path from the analysis state to the cleaning state and the second switching command 32 for returning the flow path from the cleaning state to the analysis state are automatically included in the plurality of control commands 30 to be set by the command setting processing unit 102.

Thereafter, in the case in which it is selected not to automatically set the start time and the end time by selecting the "Individual" in the time selection section 22 shown in FIG. 5 and an input operation of the time input unit 23 for inputting the start time and the end time is performed, the individual start command 36 and the individual termination command 37 are automatically included in a plurality of control commands 30 to set by the command setting processing unit 102.

The individual start command 36 is a control command 30 for executing the first switching command 31 when the input start time (for example, 60 seconds) has elapsed. Further, the individual termination command 37 is a control command 30 for executing the second switching command 32 when the input end time (for example, 3 minutes) has elapsed. The user can individually set a more appropriate start time and end time by arbitrarily setting the appropriate start time and end time by, e.g., confirming the detection result in the detector.

5. Processing when Setting Control Command

Figure 8:
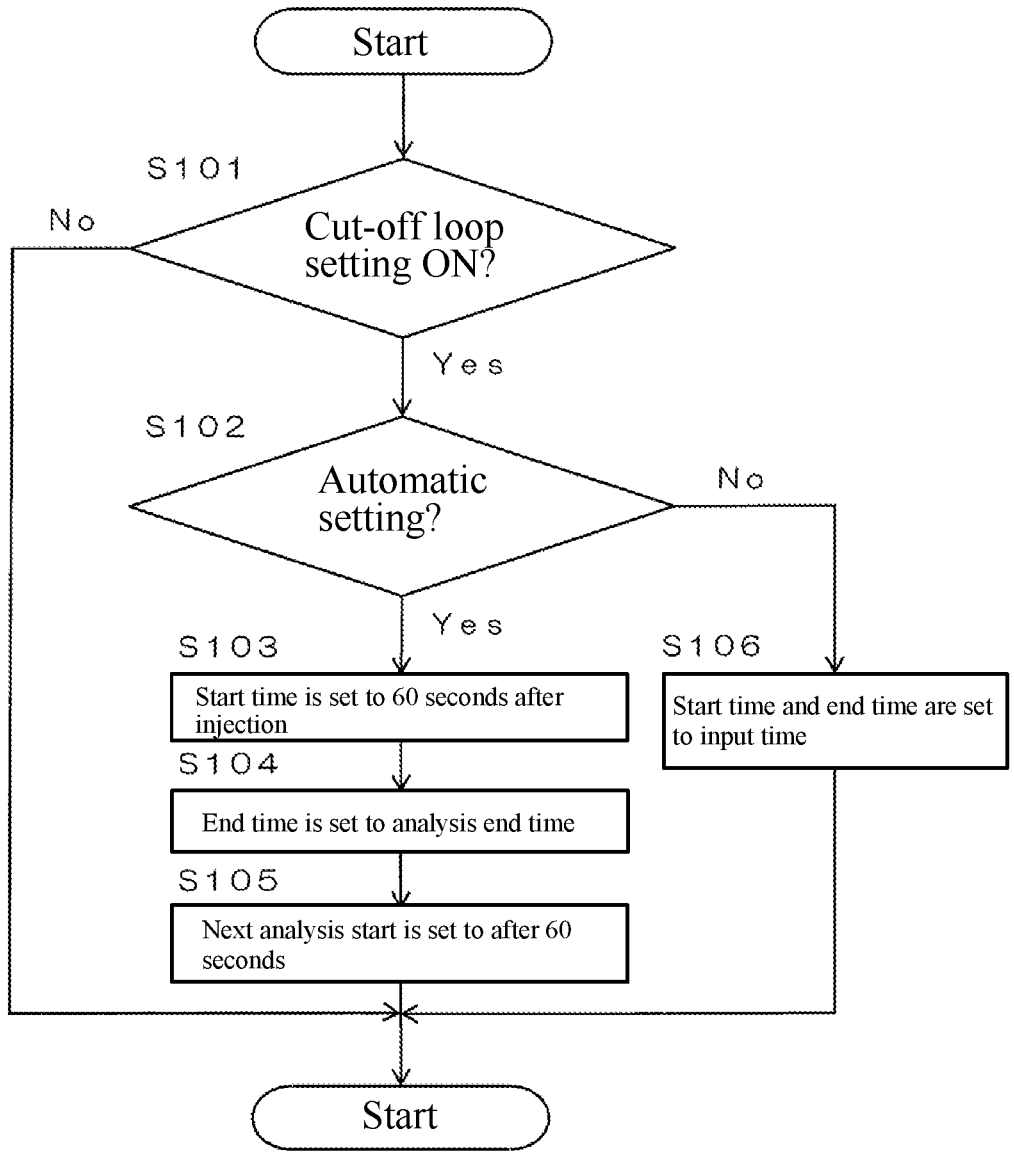
FIG. 8 is a flowchart showing one example of processing by a control unit at the time of setting control commands.

FIG. 8 is a flowchart showing one example of processing by the control unit 10 when setting the control command 30. In the setting selection section 21 shown in FIG. 5, in the case in which setting (ON setting) for setting the cut-off loop is selected (Yes in Step S101), thereafter, different processing is performed depending on whether "Automatic" or "Individual" is selected by the time selection section 22.

In the case in which "Automatic" is selected in the time selection section 22 (Yes in Step S102), the time after the lapse of 60 seconds as the first waiting time is set to the start time by the automatic start command 33 (Step S103) with respect to the time when the flow path is switched from the introduction state to the analysis state (at the time of sample injection), and the preset analysis end time is set to the end time by the automatic end command 34 (Step S104). Also, by the standby command 35, it is set so as to start the next analysis after 60 seconds as the second waiting time for the end time (Step S105).

On the other hand, in the case in which "Individual" is selected in the time selection section 22 (No in Step S102), an operation of inputting the start time and the end time to the time input unit 23 is performed. The input start time is set by the individual start command 36 with respect to the time when the flow path is switched from the introduction state to the analysis state (during sample injection), and the input end time is set by the individual termination command 37 (Step S106).

6. Modified Embodiment

In the aforementioned embodiment, the case in which the flow path switching unit 11 is configured by the six-way valve 6 was described. However, it is not limited to such a configuration. As long as the flow path can be switched to the introduction state, the analysis state, or the cleaning state, other valves may be used, or members other than valves may be used.

Further, in the aforementioned embodiment, the case in which the loop injection mechanism according to the present invention is used for a supercritical liquid chromatography was described. However, the present invention is not limited to this. For example, the present invention may be used for other analysis apparatuses such as a high performance liquid chromatograph.

DESCRIPTION OF REFERENCE SYMBOLS 1 mobile phase reservoir
2 modifier reservoir
3 first pump
4 second pump
5 mixer
6 six-way valve
7 sample loop
8 needle
9 column
10 control unit
11 flow path switching unit
12 storage unit
13 operation unit
21 setting selection section
22 time selection section
23 time input unit
30 control command
31 first switching command
32 second switching command
33 automatic start command
34 automatic end command
35 standby command
36 individual start command
37 individual termination command
101 command execution processing unit
102 command setting processing unit
103 selection acceptance processing unit
104 time input reception processing unit

The invention claimed is:
1. A loop injection mechanism comprising:
a sample loop into which a sample is introduced;
a mobile phase supply unit configured to supply a mobile phase into the sample loop;
a column into which the sample flows together with the mobile phase from the sample loop;
a flow path switching unit configured to selectively switch a flow path between an introduction state for introducing the sample in the sample loop, an analysis state for flowing the mobile phase and the sample into the column via the sample loop, and a cleaning state for introducing a cleaning solution into the sample loop to clean the sample loop and discharge the cleaning solution via a drain; and a central processing unit configured to execute a program in order to function as:
a command execution processing unit configured to execute a plurality of preset control commands;
a selection acceptance processing unit configured to accept a selection as to whether or not to switch the flow path from the analysis state to the cleaning state; and
a command setting processing unit configured to automatically include a first switching command for switching the flow path from the analysis state to the cleaning state and a second switching command for returning the flow path from the cleaning state to the analysis state in a plurality of control commands when a selection of switching the flow path from the analysis state to the cleaning state is accepted by the selection acceptance processing unit.

2. The loop injection mechanism as recited in claim 1, wherein the selection acceptance processing unit accepts, when a selection of switching the flow path from the analysis state to the cleaning state is accepted, a selection as to whether or not to automatically set a start time of switching the flow path from the analysis state to the cleaning state and an end time of returning the flow path from the cleaning state to the analysis state.

3. The loop injection mechanism as recited in claim 2, wherein the command setting processing unit automatically includes, when a selection of automatically setting the start time and the end time is accepted by the selection acceptance processing unit, an automatic start command for setting a time when a first waiting time has elapsed with respect to a time when the flow path is switched from the introduction state to the analysis state as the start time in the plurality of control commands.

4. The loop injection mechanism as recited in claim 2, wherein the command setting processing unit automatically includes, when a selection of automatically setting the start time and the end time is accepted by the selection acceptance processing unit, an automatic end command for setting a time when a preset analysis is completed as the end time in the plurality of control commands.

5. The loop injection mechanism as recited in claim 4, wherein the command setting processing unit automatically includes a standby command for starting a next analysis after a second waiting time has elapsed with respect to the end time in the plurality of control command.

6. The loop injection mechanism as recited in claim 2, wherein the central processing unit is configured to execute the program in order to function as:
a time input reception processing unit configured to accept an input of the start time and the end time when a selection of not automatically setting the start time and the end time is accepted by the selection acceptance processing unit,
wherein the command setting processing unit automatically includes, when an input of the start time and the end time is accepted by the time input reception processing unit, an individual start command for executing the first switching command when the start time has elapsed with respect to a time when the flow path is switched from the introduction state to the analysis state and an individual termination command for executing the second switching command when the end time has elapsed with respect to a time when the flow path is switched from the introduction state to the analysis state in the plurality of control commands.

7. A loop injection method comprising:
introducing a sample into a sample loop;
supplying a mobile phase into the sample loop;
supplying the sample together with the mobile phase from the sample loop to a column;
selectively switching a flow path between an introduction state for introducing the sample in the sample loop, an analysis state for flowing the mobile phase and the sample into the column via the sample loop, and a cleaning state for introducing a cleaning solution into the sample loop to clean the sample loop and discharge the cleaning solution via a drain;
executing a plurality of preset control commands;
accepting a selection as to whether or not to switch the flow path from the analysis state to the cleaning state;
including, automatically, a first switching command for switching the flow path from the analysis state to the cleaning state and a second switching command for returning the flow path from the cleaning state to the analysis state in a plurality of control commands in response to a selection of switching the flow path from the analysis state to the cleaning state being accepted.

8. The loop injection method as recited in claim 7, wherein the accepting a selection step occurs in response to:
a selection of switching the flow path from the analysis state to the cleaning state, a selection as to whether or not to automatically set a start time of switching the flow path from the analysis state to the cleaning state, and an end time of returning the flow path from the cleaning state to the analysis state.

9. The loop injection method as recited in claim 8, wherein the including step automatically includes, when a selection of automatically setting the start time and the end time is accepted, an automatic start command for setting a time when a first waiting time has elapsed with respect to a time when the flow path is switched from the introduction state to the analysis state as the start time in the plurality of control commands.

10. The loop injection method as recited in claim 8, wherein the including step automatically includes a selection of automatically setting the start time and the end time and an end command for setting a time when a preset analysis is completed as the end time in the plurality of control commands.

11. The loop injection method as recited in claim 10, wherein the including step automatically includes a standby command for starting a next analysis after a second waiting time has elapsed with respect to the end time in the plurality of control commands.

12. The loop injection method as recited in claim 8, further comprising:
accepting an input of the start time and the end time when a selection of not automatically setting the start time and the end time is accepted by the accepting a selection step,
wherein the including step comprises:
an individual start command for executing the first switching command when the start time has elapsed with respect to a time when the flow path is switched from the introduction state to the analysis state in response to an input of the start time and the end time being accepted; and
an individual termination command for executing the second switching command when the end time has elapsed with respect to a time when the flow path is switched from the introduction state to the analysis state in the plurality of control commands.

* * * * *